US006945956B2

(12) United States Patent
Waldhauser et al.

(10) Patent No.: US 6,945,956 B2
(45) Date of Patent: Sep. 20, 2005

(54) STEERABLE CATHETER

(75) Inventors: Steven L. Waldhauser, Circle Pines, MN (US); James R. Skarda, Lake Elmo, MN (US); Jeffrey B. Geske, Fridley, MN (US); Gregory P. Shipe, Plymouth, MN (US); Eduard T. Teisanu, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 291 days.

(21) Appl. No.: 10/328,329

(22) Filed: Dec. 23, 2002

(65) Prior Publication Data

US 2004/0122360 A1 Jun. 24, 2004

(51) Int. Cl.[7] ............................................... A61M 37/00
(52) U.S. Cl. .................................................... 604/95.01
(58) Field of Search .............................. 604/523, 95.01, 604/264, 530, 528, 532, 524–527; 606/32; 138/103, 120, 124, 132

(56) References Cited

U.S. PATENT DOCUMENTS

| | | | | |
|---|---|---|---|---|
| 2,688,329 | A | | 9/1954 | Wallace |
| 3,605,725 | A | | 9/1971 | Bentov |
| 4,586,923 | A | | 5/1986 | Gould et al. |
| 5,030,204 | A | | 7/1991 | Badger et al. |
| 5,168,864 | A | * | 12/1992 | Shockey ..................... 600/144 |
| 5,431,168 | A | | 7/1995 | Webster |
| 5,445,148 | A | | 8/1995 | Jaraczewski et al. |
| 5,484,407 | A | | 1/1996 | Osypka |
| 5,487,757 | A | | 1/1996 | Truckai et al. |
| 5,545,200 | A | | 8/1996 | West et al. |
| 5,571,085 | A | | 11/1996 | Accisano |
| 5,738,742 | A | | 4/1998 | Stevens |
| 5,792,124 | A | | 8/1998 | Horrigan et al. |
| 5,823,955 | A | | 10/1998 | Kuck et al. |
| 5,964,971 | A | | 10/1999 | Lunn |
| 6,002,955 | A | | 12/1999 | Willems et al. |
| 6,171,277 | B1 | | 1/2001 | Ponzi et al. |
| 6,217,549 | B1 | | 4/2001 | Selmon et al. |
| 6,251,092 | B1 | * | 6/2001 | Qin et al. ................ 604/95.01 |
| 6,371,476 | B2 | | 4/2002 | Isogai et al. |
| 6,482,221 | B1 | | 11/2002 | Hebert et al. |
| 6,595,982 | B2 | * | 7/2003 | Sekino et al. ............... 604/524 |
| 6,702,782 | B2 | * | 3/2004 | Miller et al. ............. 604/96.01 |
| 2001/0005552 | A1 | | 6/2001 | Berg et al. |
| 2001/0049491 | A1 | | 12/2001 | Shimada et al. |
| 2002/0040232 | A1 | | 4/2002 | Divino et al. |
| 2002/0111643 | A1 | | 8/2002 | Shuman et al. |
| 2003/0236492 | A1 | | 12/2003 | Honebrink |

FOREIGN PATENT DOCUMENTS

| | | |
|---|---|---|
| JP | 7051378 | 2/1995 |

* cited by examiner

*Primary Examiner*—Manuel Mendez
(74) *Attorney, Agent, or Firm*—Girma Wolde-Michael; Daniel G. Chapile

(57) ABSTRACT

A steerable catheter and methods of fabrication including a catheter body formed of a continuous wire braid formed of wires braided over a delivery lumen liner and a pull wire lumen liner distal to a pull wire jacket port, braided around the pull wire jacket port to form a braid port, and over at least a portion of the delivery lumen liner proximal to the pull wire jacket port. A pull wire extends from a pull wire proximal end through the pull wire lumen port and through the pull wire lumen to a pull wire distal end. A band is attached to the pull wire distal end and fitted over a distal segment of the wire braid proximal to the catheter body distal end to fix the pull wire distal end to the catheter body and restrain the wire distal end from flaring away from the delivery lumen liner.

14 Claims, 8 Drawing Sheets

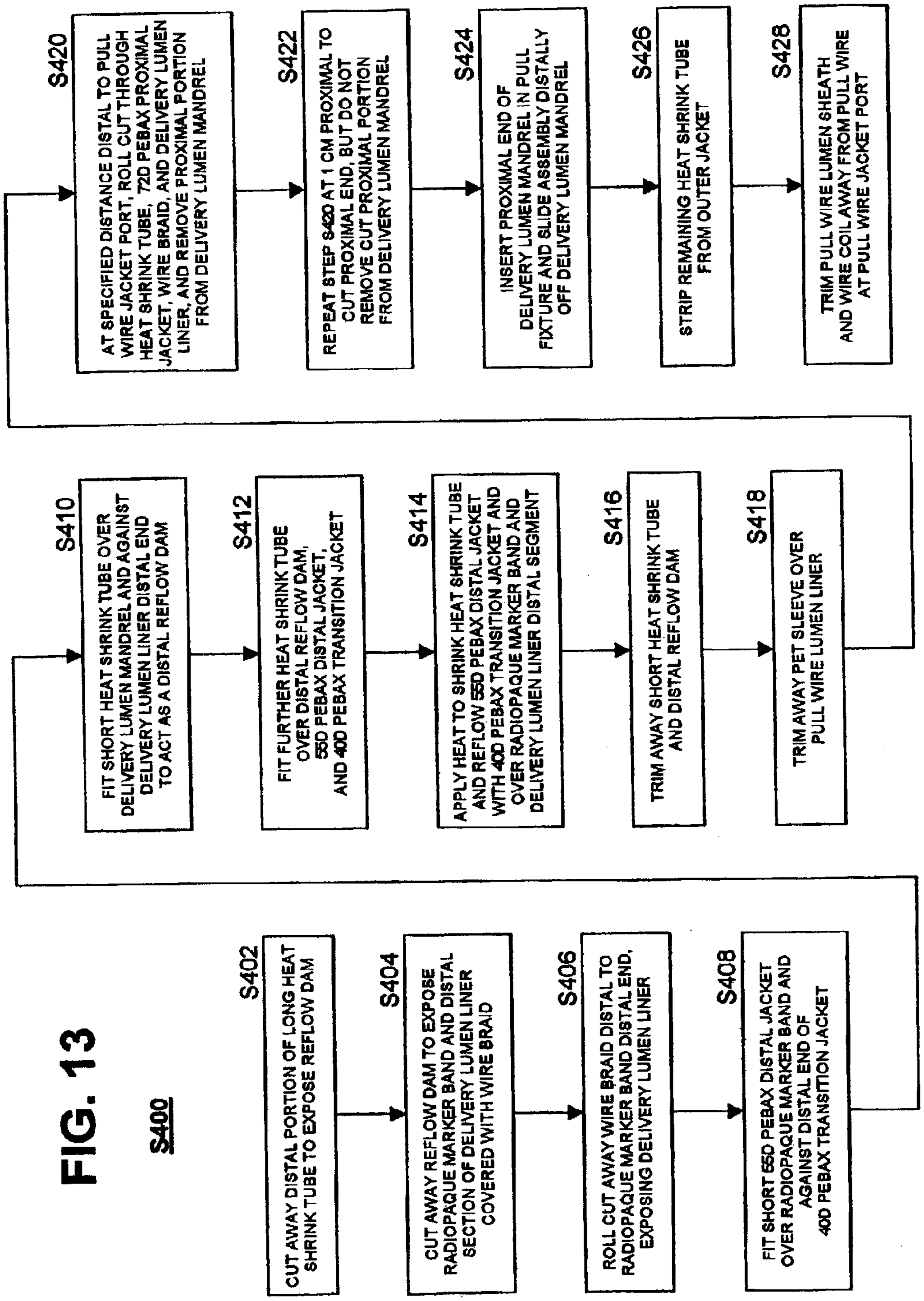

S400: CUT AWAY DISTAL PORTION OF LONG HEAT SHRINK TUBE TO EXPOSE REFLOW DAM

→ S402: CUT AWAY REFLOW DAM TO EXPOSE RADIOPAQUE MARKER BAND AND DISTAL SECTION OF DELIVERY LUMEN LINER COVERED WITH WIRE BRAID

→ S404: ROLL CUT AWAY WIRE BRAID DISTAL TO RADIOPAQUE MARKER BAND DISTAL END, EXPOSING DELIVERY LUMEN LINER

→ S406: FIT SHORT 55D PEBAX DISTAL JACKET OVER RADIOPAQUE MARKER BAND AND AGAINST DISTAL END OF 40D PEBAX TRANSITION JACKET

→ S408 (continues)

→ S410: FIT SHORT HEAT SHRINK TUBE OVER DELIVERY LUMEN MANDREL AND AGAINST DELIVERY LUMEN LINER DISTAL END TO ACT AS A DISTAL REFLOW DAM

→ S412: FIT FURTHER HEAT SHRINK TUBE OVER DISTAL REFLOW DAM, 55D PEBAX DISTAL JACKET, AND 40D PEBAX TRANSITION JACKET

→ S414: APPLY HEAT TO SHRINK HEAT SHRINK TUBE AND REFLOW 55D PEBAX DISTAL JACKET WITH 40D PEBAX TRANSITION JACKET AND OVER RADIOPAQUE MARKER BAND AND DELIVERY LUMEN LINER DISTAL SEGMENT

→ S416: TRIM AWAY SHORT HEAT SHRINK TUBE AND DISTAL REFLOW DAM

→ S418: TRIM AWAY PET SLEEVE OVER PULL WIRE LUMEN LINER

→ S420: AT SPECIFIED DISTANCE DISTAL TO PULL WIRE JACKET PORT, ROLL CUT THROUGH HEAT SHRINK TUBE, 72D PEBAX PROXIMAL JACKET, WIRE BRAID, AND DELIVERY LUMEN LINER, AND REMOVE PROXIMAL PORTION FROM DELIVERY LUMEN MANDREL

→ S422: REPEAT STEP S420 AT 1 CM PROXIMAL TO CUT PROXIMAL END, BUT DO NOT REMOVE CUT PROXIMAL PORTION FROM DELIVERY LUMEN MANDREL

→ S424: INSERT PROXIMAL END OF DELIVERY LUMEN MANDREL IN PULL FIXTURE AND SLIDE ASSEMBLY DISTALLY OFF DELIVERY LUMEN MANDREL

→ S426: STRIP REMAINING HEAT SHRINK TUBE FROM OUTER JACKET

→ S428: TRIM PULL WIRE LUMEN SHEATH AND WIRE COIL AWAY FROM PULL WIRE AT PULL WIRE JACKET PORT

STEERABLE CATHETER

FIELD OF THE INVENTION

The present invention relates generally to elongated multi-lumen medical devices adapted to be inserted through an access pathway into a body vessel, organ or cavity to locate a therapeutic or diagnostic distal segment of the elongated medical device into alignment with an anatomic feature of interest, and particularly to a steerable bilumen catheter having a leak resistant delivery lumen.

BACKGROUND OF THE INVENTION

Many elongated medical devices are known that are inserted through an access pathway into a body vessel, organ or cavity to locate a therapeutic or diagnostic distal segment of the elongated medical device into alignment with an anatomic feature of interest. For example, catheters, introducers and guide sheaths of various types, drainage tubes, and cannulas are available that extend from outside the body through an access pathway to a site of interest and provide a lumen through which fluids, materials, or other elongated medical devices are introduced to the site or body fluids are drained or sampled from the site. Other elongated medical devices include many forms of medical electrical leads that bear sensing and/or electrical stimulation electrodes for sensing electrical signals of the body and/or applying electrical stimulation to the body, e.g. leads for pacing, cardioversion, nerve stimulation, muscle stimulation, spinal column stimulation, deep brain stimulation, etc. Other medical electrical leads bearing physiologic sensors for measuring pressure, temperature, pH, etc, in a distal segment thereof that are adapted to be placed at a site of interest are also known. Other elongated medical devices include guidewires that are directed through tortuous vascular pathways to locate a distal segment thereof typically within a blood vessel. A catheter, e.g. a PTCA balloon catheter for dilating constrictions in blood vessels or delivering stents and grafts or a medical electrical lead having a through-lumen are then advanced over-the-wire to the site. Other elongated medical devices include stiffening stylets that are placed into the lumens of medical electrical leads and in certain guidewires to impart column strength and stiffness to the assembly to enable transvenous advancement into a heart chamber or cardiac blood vessel.

Such elongated medical devices must have flexibility to navigate the twists and turns of the access pathway, sufficient column strength in the proximal segment thereof to be pushed through the access pathway alone, over a guidewire, or through a lumen, and the capability of orienting the distal segment and any electrodes, sensors or ports of the distal segment in a preferred alignment with an anatomical feature at the accessed site so that a diagnostic or therapeutic procedure can be completed. In general terms, the elongated medical device body must also resist kinking and be capable of being advanced through access pathways that twist and turn, sometimes abruptly at acute angles.

It is commonly the practice, particularly with guide and diagnostic catheters, to provide pre-formed bends at the junctions between segments, or pre-curved or shaped segments that are adapted to orient the distal segment and possibly intermediate segments into alignment with an anatomical feature at the accessed site. For instance, many diagnostic procedures involve placing a catheter tip into a side port and across a vascular orifice to inject radiographic fluid through the catheter lumen into the vessel. Such diagnostic catheters have historically been formed of thermoplastic materials that can be heated by being inserted within heated water, for example, and bent into a shape that the physician can use in attempting to access the vessel opening. A considerable variety of pre-formed shapes of such catheters have been developed over the years and made available for use in such procedures. Still, the physician may find that the anatomy of any given patient may require altering the pre-formed bend by heating the catheter, changing the bend and letting it cool before it is advanced to the site where it must make an abrupt change in direction.

The distal segment of the guide catheter frequently needs to be selectively deflected or bent and straightened again while being advanced within the patient to steer the catheter distal end into a desired body lumen or chamber. Various steerable mechanisms have been disclosed to steer guide catheters and other elongated medical devices, involving use of a deflection mechanism, referred to as control lines, reins, deflection wires, traction wires, push-pull wires or pull wires (herein “pull wires”), extending between a proximal handle through proximal and distal segments of the catheter body to a point of attachment of the pull wire distal end to the distal segment. More complex steerable catheters have two or more pull wire lumens and pull wires extending from the handle through the pull wire lumens to different points along the length or about the circumference of the catheter body to induce bends in multiple segments of the catheter body and/or in different directions. The deflection mechanism is manipulated to selectively deflect or straighten the distal segment and, in some cases, intermediate segments of the device body.

Exemplary multi-lumen and bilumen catheters having relatively larger delivery lumens and incorporating pull wires in relatively small pull wire lumens extending alongside the delivery lumens to selectively deflect the distal segment of the catheter are disclosed in U.S. Pat. Nos. 2,688,329, 3,605,725, 4,586,923, 5,030,204, 5,431,168, 5,484,407, 5,571,085, 6,217,549, 6,251,092, and 6,371,476, and in published U.S. Patent Appln. Pub. No. 2001/0049491 assigned to Biotran Corp. Many such steerable catheters are relatively simple, having only a pull wire lumen and a delivery lumen extending between proximal and distal lumen ports for introduction or withdrawal of fluids, or delivery of drugs or other medical devices into the body. Other steerable catheters are more complex, typically incorporating one or more distal electrode and corresponding conductor, and sometimes including other sensors, inflatable balloons, and other components.

For example, many versions of electrophysiology (EP) catheters have been disclosed that are designed to perform mapping and/or ablation of cardiac tissue to diagnose and treat abnormal tissue that induces or sustains cardiac arrhythmias and that employ deflectable distal and intermediate segments controlled by push-pull or pull wire mechanisms. During an EP ablation or mapping procedure, the guide catheter must be maneuvered through a patient’s branched vasculature to advance an EP device into a patient’s coronary sinus. The steerable distal end of the guide catheter is used to orient the distal tip of the EP device with respect to tissue, such as a patient’s endocardium, to facilitate proper delivery of the device’s RF or laser energy to the tissue. Highly complex shapes are sometimes found necessary to encircle a pulmonary vein orifice, for example, to ablate the left atrial wall tissue to interrupt arrhythmic pathways. For example, commonly assigned U.S. Pat. Nos. 5,445,148, 5,545,200, 5,487,757, 5,823,955, and 6,002,955 disclose a variety of such shapes and mechanisms for forming the shapes.

A relatively large diameter delivery lumen and relatively small diameter pull wire lumen(s) (as well as other lumens for conductors or the like) are desirable in such steerable catheters. However, the outer diameter of the steerable catheter must be minimized so that the steerable catheter can be readily advanced within the patient without trauma. Therefore extrusion techniques used to fabricate relatively large diameter, thick walled, multi-lumen fluid drainage or hemodialysis catheters and early steerable catheters, e.g., that are disclosed in the above-referenced '725 patent, are inappropriate. The walls of multi-lumen steerable catheters are necessarily thin in order to maximize the size of the delivery lumen and minimize the outer diameter of the guide catheter, while at the same time having properties that enable the catheter to exhibit column strength and pushability.

Therefore, a tubular or braided wire reinforcement is employed within at least a proximal segment of the outer wall or sheath of the typical steerable catheter to stiffen the thin catheter wall as disclosed in many of the above-referenced patents and in commonly assigned U.S. Pat. Nos. 5,738,742 and 5,964,971. The wire braid catheter wall enables torque transmission to the catheter distal end as the proximal end of the catheter outside the patient is rotated.

In the fabrication of such steerable catheters, it is necessary to extend the pull wire from a distal point of attachment proximally through the pull wire lumen extending through the steerable distal segment and the non-deflectable proximal segment of the catheter body to an exit point where the pull wire is routed through the outer sheath of the catheter body so that the pull wire proximal end can be coupled to a steering mechanism of the handle. The proximal ends of the pull wires of such steerable catheters either exit through the sidewall of the catheter body at a point distal to the catheter body proximal end, as shown in the above-referenced '030 patent and Biotran publication, or from a proximal end opening of the catheter body and are attached to a handle to be manipulated in use to induce a bend or to straighten the deflectable distal segment of the catheter body. Thus, the handle usually encloses the portion of the catheter body where the proximal end of the pull wire is exposed, and the pull wire proximal end is attached to a pull wire knob or ring that can be manipulated by the user to induce a deflection in the catheter body distal segment to steer it.

Some steerable bilumen or multilumen catheters are employed to access sites in the heart chambers, cardiac vessels or other vessels or organs of the body to deliver drugs, diagnostic agents, medical devices, and pressurized fluids, e.g., saline, to treat or cool tissue through the delivery lumen. In certain cases, electrical energy is delivered to tissue from electrodes incorporated into the catheter body or from electrodes of an electrical medical lead advanced through the delivery lumen to the site. The integrity of the delivery lumen is very important to these uses. We have found that when the delivery lumen is filled with pressurized fluid, particularly, to weep fluid from a porous irrigation tip closing the delivery lumen exit port or otherwise provide irrigation at an electrode site, the fluid can leak through the wall of the delivery lumen unless the integrity and strength of the delivery lumen wall is assured. Pressurized saline within the delivery lumen could leak into the pull wire lumen, travel proximally in the pull wire lumen, and be ejected into the handle. In the context of use of the steerable catheter body in a cautery or an EP catheter, the leakage of saline into the handle can short out electrical connections therein and/or present a risk of electrical shock to the user if the saline is in contact with the cautery or ablation electrodes.

This concern about leakage is exacerbated if the proximal exit of the pull wire from the catheter body is made through a sidewall lumen port formed in the sidewall of the catheter body distal to the catheter body proximal end. Such a sidewall lumen port is desirable when the catheter body is joined to certain bilumen catheter hubs or handles.

Once the bilumen catheter body is fabricated, it is necessary to form the sidewall lumen port through the intact catheter body sidewall before the pull wire can be inserted into the pull wire lumen (with or without a pull wire lumen liner or coiled wire sheath defining the pull wire lumen). The sidewall lumen port is made from the outside into the pull wire lumen by cutting or drilling through the outer thermoplastic layer, the wire braid, the inner thermoplastic layer, and any wire coil or pull wire lumen liner that is used (unless the incision is made proximal to the proximal end of the wire coil or pull wire lumen liner). Making such an incision is difficult, and there is a significant probability that an error may be made and that the delivery lumen liner can be punctured. The puncture may not be detectable until the delivery lumen is filled with high-pressure fluid, and the fluid leaks through the sidewall or through the pull wire lumen extending into the handle.

Even if the sidewall lumen port is successfully made, it is still difficult to route a long pull wire inserted proximal end first into the pull wire lumen distal end opening and then to route the pull wire proximal end out through the sidewall lumen port.

These fabrication steps do not lend themselves to automation and consequently require expensive, skilled hand labor, a significant expenditure of time, and can still result in high scrap at every stage of manufacturing, low productivity, and catheter products of uneven quality and reliability. Consequently, there is a need for improved manufacturing methods that can be automated at least in part and that simplifies fabrication, reduces fabrication time, cost, and scrap and that results in high quality multi-lumen catheter bodies having uniform appearance and handling characteristics. Similarly there is a need for a design of such steerable catheters that is highly robust to ensure the integrity of the delivery lumen, the reliability of use of the pull wire, and to provide consistent bend radii and shapes in the distal segments. The present invention satisfies these and other needs.

SUMMARY OF THE INVENTION

The present invention is directed to an elongated steerable catheter for introduction into a patient's body that is robust in design and manufacture including an elongated catheter body extending between catheter body proximal and distal ends, a catheter body axis, and at least a delivery lumen and a pull wire lumen. The pull wire lumen is defined by a pull wire lumen liner that extends from a pull wire lumen liner distal end near the catheter body distal end proximally through the catheter body and through a pull wire jacket port through the sidewall of the catheter body located distally to the catheter body proximal end. The delivery lumen is defined by a delivery lumen liner that extends between a delivery lumen entry port at the catheter body proximal end and a delivery lumen exit port at the catheter body distal end. The catheter body is reinforced at least in part by a wire braid that is braided over the delivery lumen liner and the pull wire lumen liner distal to the delivery lumen entry port, around the pull wire jacket port and then over the delivery lumen liner proximal to the delivery lumen exit port.

In a first aspect of the present invention, a sub-assembly of the catheter body including the delivery lumen liner and the pull wire lumen liner are braided with a wire braid having a proximal segment of the pull wire extending through a braid port of the wire braid in the sidewall of the sub-assembly. Wire strands are braided over the delivery lumen liner and the pull wire lumen liner as they are fed simultaneously through a wire braider so that the liners are arranged side-by-side to form a distal segment of the sub-assembly. The pull wire lumen liner is diverted away from delivery lumen liner at a point where the pull wire jacket port is to be formed. The wire strands are braided around the perimeter of the pull wire lumen liner to form a braid port and then over the proximal segment of the delivery lumen liner to the catheter body proximal end. Thus, the intact wire braid extends around only the delivery lumen liner in a proximal segment of the sub-assembly and around both the delivery lumen liner and the pull wire lumen liner in a distal segment of the sub-assembly.

In a second aspect of the invention, a high tensile strength wire is employed to form the wire braid woven about the pull wire lumen liner and/or the delivery lumen liner that is entrapped mechanically at the catheter body distal end. Torqueability of the catheter body through the entire wire braid reinforced catheter body length is not negatively affected by annealing the wire braid during the fabrication process, since annealing is not necessary. More particularly, a band attached to the pull wire distal end is fitted over a distal segment of the wire braid and adhered with the wire braid prior to formation of the outer jacket of the catheter body. The band therefore entraps and prevents the wires at the distal end segment of the wire braid from flaring away from the delivery lumen liner and secures the pull wire distal end to the catheter body. The band is preferably radiopaque to provide a marker band visible under fluoroscopy.

In this way, the wire-braided sub-assembly is formed of the delivery lumen liner and the pull wire lumen liner tightly wound together in the distal segment with the wire braid thereby avoiding the need to anneal the wire ends, minimizing manual handling of the parts, minimizing the diameter of the wire-braided sub-assembly and avoiding bunching of the wire braid and twisting of the wire braid and/or the lumen liners, and resulting in a uniform sub-assembly that is readily testable for defects. Moreover, the braid port is prepared through the wire braid that the proximal segment of the pull wire lumen liner extends through, eliminating the need to dissect through the wire braid to access the pull wire lumen.

During fabrication of the wire-braided sub-assembly, the delivery lumen is supported by a delivery lumen mandrel, and the pull wire lumen is supported by a pull wire lumen mandrel inserted into the wire coil. During wire braiding, the proximal segment of the pull wire sheath and wire coil are protected by insertion into a further protective tube, e.g., a stainless steel tube, so that the braided wire only contacts the protective tube as the wire is braided around the protective tube to form the braid port. When braiding is completed, the protective tube is removed, and the pull wire lumen mandrel is withdrawn from the pull wire lumen, and the proximal end of the pull wire is inserted through the pull wire lumen distal end opening until the radiopaque marker band welded to the pull wire distal end can be placed over the wire braid proximal to the catheter body distal end.

In a particular embodiment of the invention, the pull wire lumen liner is formed of a wire coil disposed within the lumen of a pull wire lumen sheath. Preferably, the wire coil turns are closely wound except for a distal segment corresponding in length with the length of the distal segment of the catheter body adapted to be bent into a curved shape by tensioning the pull wire where the wire coil turns are space wound. The uniform diameter and the hard surface of the wire coil lumen facilitate the insertion of the pull wire through its length and out of the braid port.

In a further aspect of the invention, the sub-assembly is encapsulated in a reflow encapsulation process to form a polymeric outer sheath reinforced by the wire braid and embedding the delivery lumen liner and the distal segment of the delivery lumen liner. The delivery lumen mandrel remains in the delivery lumen and the pull wire remains in the pull wire lumen during encapsulation of the sub-assembly to form the outer jacket. In this way, the pull wire is already present during the encapsulation. It is not necessary to remove a separate pull wire lumen mandrel from the encapsulation to form the pull wire lumen, and it is not necessary to later insert the pull wire into the pull wire lumen.

In general terms, the sub-assembly is encased in such a polymeric outer sheath formed of a series of thermoplastic tubular jackets having durometers that are progressively softer distally that are inserted over the proximal and distal segments of the sub-assembly. A high melting point heat shrink tube is fitted over the jackets and heat is applied to shrink the heat shrink tube and melt the thermoplastic material through the wire braid and around the delivery lumen liner in the proximal segment of the sub-assembly and around the delivery lumen liner and the pull wire lumen liner in the distal segment of the sub-assembly.

Advantageously, holes can be made through the sidewalls of the thermoplastic jacket and the overlying heat shrink tube that are to be positioned to overlie the braid port and that are large enough so that the pull wire lumen liner and the pull wire within the pull wire lumen can be inserted through the aligned sidewall holes before reflow melting of the thermoplastic jacket. Mistakes in making the sidewall holes simply result in scrapping the inexpensive jacket and heat shrink tube. Moreover, the sidewall holes can be preformed in an automated assembly. This avoids the potential leakage problems attendant to the prior art practice of cutting through the outer jacket to locate the pull wire lumen.

In preparation for encapsulation, the proximal jacket is slipped within the lumen of the heat shrink tube, and the holes in the sidewalls of the proximal jacket and the heat shrink tube are aligned. The proximal ends of the pull wire, the pull wire lumen sheath and the wire coil are inserted through the thermoplastic jacket lumen and then out of the holes formed in the sidewalls of the thermoplastic jacket and the heat shrink tube. Thus, a thermoplastic proximal jacket can be slipped over the proximal segment of the sub-assembly and proximal portion of the distal segment of the sub-assembly while drawing the pull wire out of the hole formed in the sidewalls of the thermoplastic proximal jacket and the heat shrink tube until the holes are aligned with the braid port.

Further steps are taken to place a thermoplastic intermediate jacket and a thermoplastic transition jacket (located between the proximal and intermediate jackets) within the elongated heat shrink tube lumen. Heat is then applied to shrink the heat shrink tube and melt the thermoplastic proximal, transition and intermediate jackets within the heat shrink tube lumen in a reflow encapsulation process. The melted thermoplastic polymers flow through the wire braid and around the pull wire lumen and/or delivery lumen liners. The pull wire lumen sheath of the pull wire lumen liner prevents flow of melted polymer into the wire coil defining the pull wire lumen. A further reflow process is employed to melt a distal jacket of thermoplastic material and encapsulate the distal radiopaque band and distal section of the delivery lumen liner. When the encapsulation is completed, the pull wire lumen sheath and wire coil can be cut away carefully at the pull wire jacket port to expose a proximal length of the pull wire.

The resulting catheter bodies are typically coupled to a proximal handle or hub having a movable element coupled to the pull wire proximal end that the user manipulates to selectively apply tension to induce a bend in the catheter body distal segment or to release tension on the pull wire to allow the catheter body distal segment to straighten. In practice, the applied tension causes the movable element and the catheter body proximal end to separate apart.

In certain catheters, the delivery lumen exit port can be blocked by porous or irrigated tip segments to allow the delivery lumen to be filled with pressurized fluid that weeps through microscopic holes in the RF electrode or tip to irrigate a site in the body that is accessed by manipulation of the pull wire in the manner of the Medtronic® Sprinkler® RF ablation catheter.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent from the following description in which the preferred embodiments are disclosed in detail in conjunction with the accompanying drawings in which:

FIG. 13 is a detailed flow chart illustrating the steps of step S400 of FIG. 9.

DETAILED DESCRIPTION OF THE PREFERRED EMBODIMENTS

The present invention may be implemented in a wide variety of elongated steerable catheters to facilitate advancement of the catheter body distal end through constricted and twisting access pathways, including the vascular system, of the human body and/or to alignment of a catheter body into conformance with an anatomical structure of interest.

The present invention can be implemented in catheters having at least two lumens or multiple lumens extending the length of the catheter body. For convenience, the illustrated preferred embodiments depict steerable catheters having at least one delivery lumen and a pull wire lumen that can receive a pull wire to induce bends and curves in at least an intermediate section of the catheter body.

Figure 1:
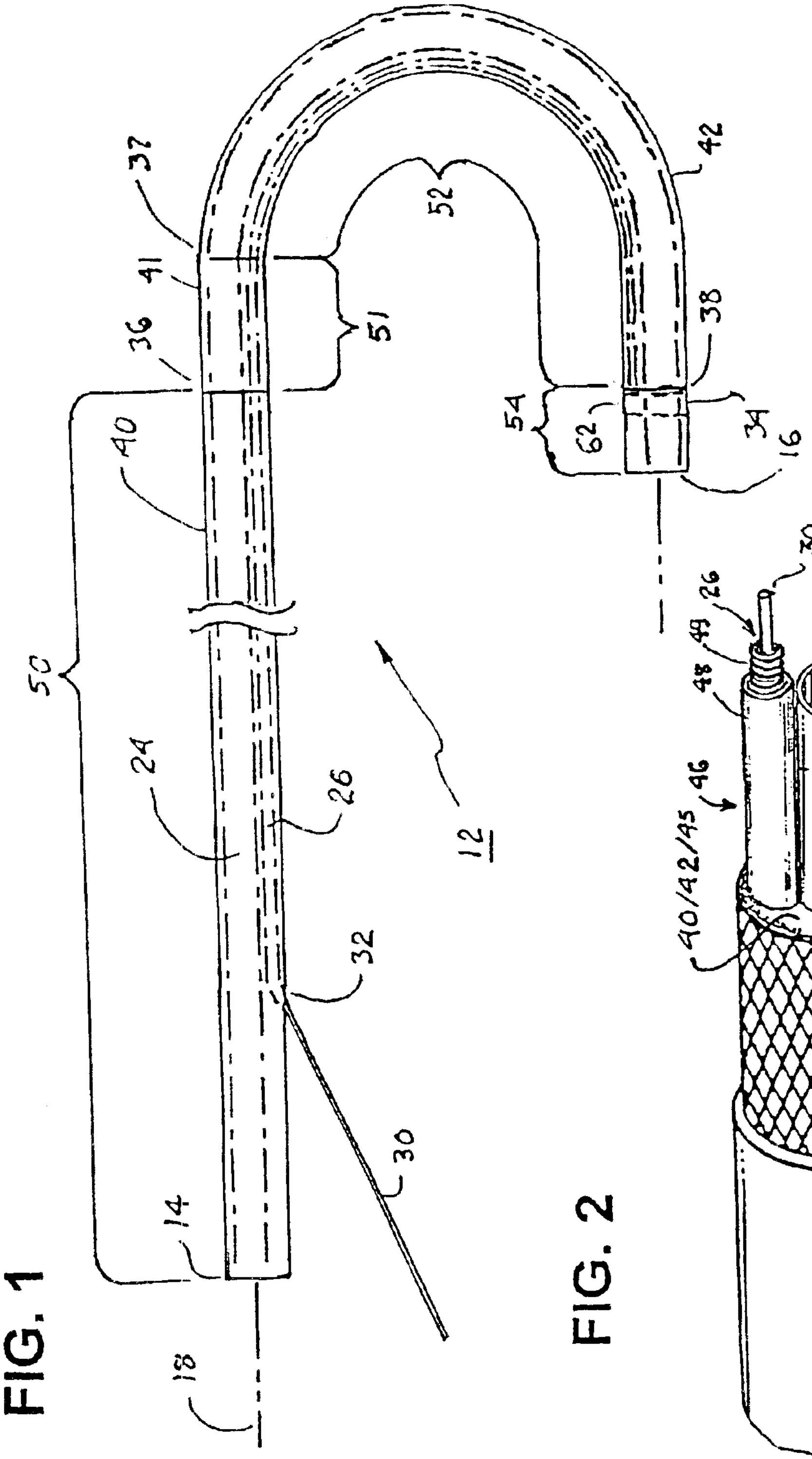
FIG. 1 is a plan view of a catheter body that the present invention is advantageously incorporated into.

Thus, the present invention is described in the context of a steerable catheter, and several embodiments are described herein by way of example. First, a multi-lumen catheter body 12 that may incorporate the concepts of this invention is shown in FIG. 1 with a bend induced in the intermediate section 52 thereof. The elongated catheter body 12 has a catheter axis 18 and extends from a catheter body proximal end 14 adapted to be coupled with a catheter hub to a catheter body distal end 16. A delivery lumen 24 extends through the catheter body 12 from a delivery lumen proximal end opening or entry port at the catheter body proximal end 14 to a delivery lumen distal end opening or exit port at the catheter body distal end 16. A pull wire lumen 26 extends alongside the delivery lumen 24 through the catheter body 12 from a pull wire lumen proximal end opening or entry port 32 through the sidewall of the catheter body 12 and a pull wire lumen closed distal end proximal to the catheter body distal end 16, particularly, proximal to the junction 38. A pull wire 30 extends from a pull wire proximal end through the pull wire jacket port 32 and through the pull wire lumen 26 to a pull wire distal end fixed to the catheter body 12 at the pull wire lumen distal end as described further herein.

Generally speaking, the catheter body 12 includes a number of body sections, e.g., body sections 50, 52 and 54, and a transition section 51 along its length formed of different materials and structural components to provide different handling characteristics. The sections 50, 51, and 52 are formed of respective outer sheath segments or jackets 40, 41, and 42 of thermoplastic materials that contribute to making the most proximal section 50 relatively stiff to impart column strength and torqueability and to making intermediate section 52 more flexible and bendable upon tensioning of the pull wire 30. The transition section 51 is less stiff than the proximal section 50 but stiffer than the intermediate section 52. The distal section 54 incorporates a soft jacket 34 of thermoplastic material that is intended to be atraumatic at catheter body distal end 16 to avoid injury to tissue as described in the above-referenced ’092 patent, for example. A further short transition jacket of thermoplastic materials may be reflow molded bridging junction 38.

The number of such body sections and the length and stiffness and composition of each such body sections can be specified to suit the particular use and dimensions of the catheter body 12. Such specifications are not essential to the practice of the present invention, and the catheter body 12 described herein is merely illustrative of one preferred embodiment of a suitable catheter body.

Figure 2:
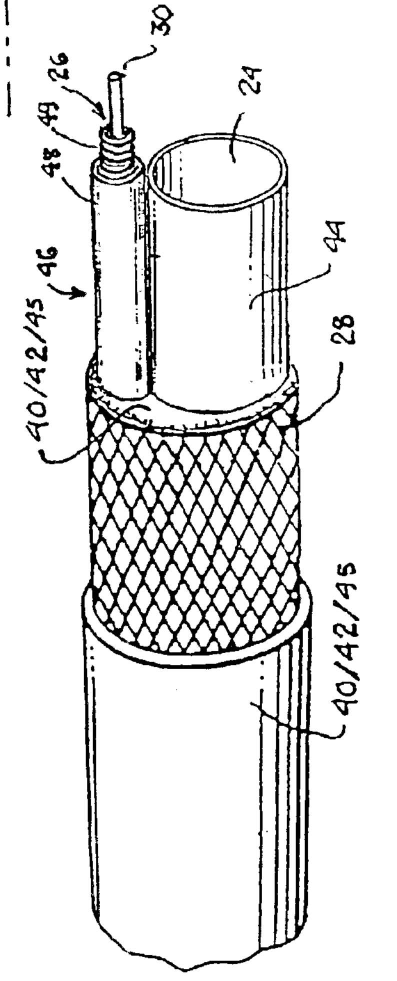
FIG. 2 is a perspective view of a section of the catheter body of FIG. 1 illustrating the internally disposed wire braid overlying the side-by-side aligned deflection lumen and delivery lumen.

As shown in FIG. 2, the catheter body 12 within the proximal section 50 distal to the pull wire jacket port 32, within the transition section 51, and within the intermediate section 52 is formed of a proximal jacket 40 or a transition jacket 41 or an intermediate jacket 42 encasing or encapsulating a tubular wire braid 28, a delivery lumen liner 44 defining delivery lumen 24, and a pull wire lumen liner 46 defining the pull wire lumen 26. Delivery lumen liner 46 preferably comprises a pull wire lumen sheath 48 and a wire coil 49 described further below. The delivery and pull wire lumen liners 44 and 46 may have a substantially uniform cross-sectional area along the lengths thereof or may vary along the lengths thereof. It is desirable for the catheter body 12 to be constructed to assure that the delivery and pull wire lumens 24 and 26 maintain their cross-sectional shape and to provide the desired flexibility, pushability, torqueability and low profile of the catheter body 12 required for its intended use in a steerable catheter. It is further desirable that the inner surfaces of the lumen liners 44 and 46 are lubricious to enable free passage or movement of devices therethrough. It is also desirable that the lumen liners 44 and 46 resist rupture or penetration.

Figure 6:
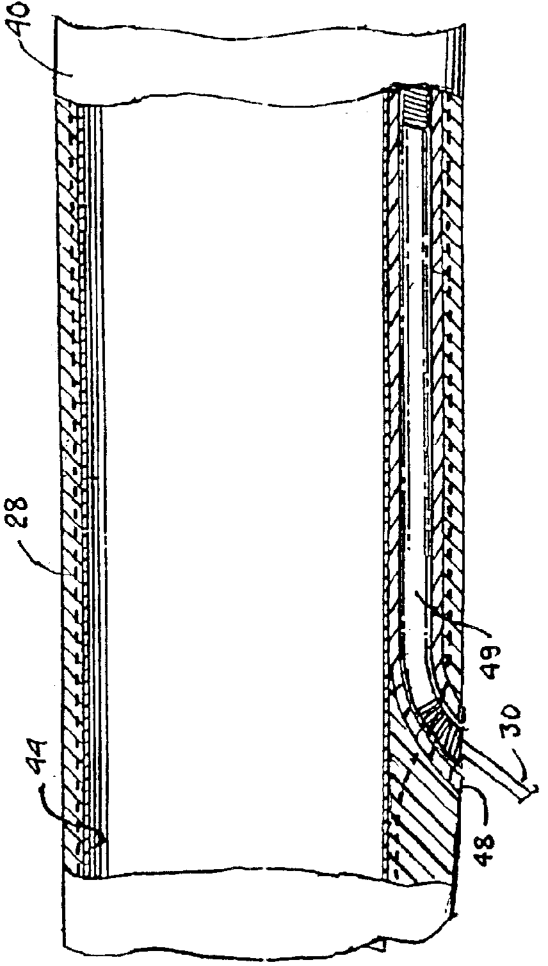
FIG. 6 is a cross-section view of a portion of the proximal section of the catheter body showing the pull wire jacket port.
Figure 7:
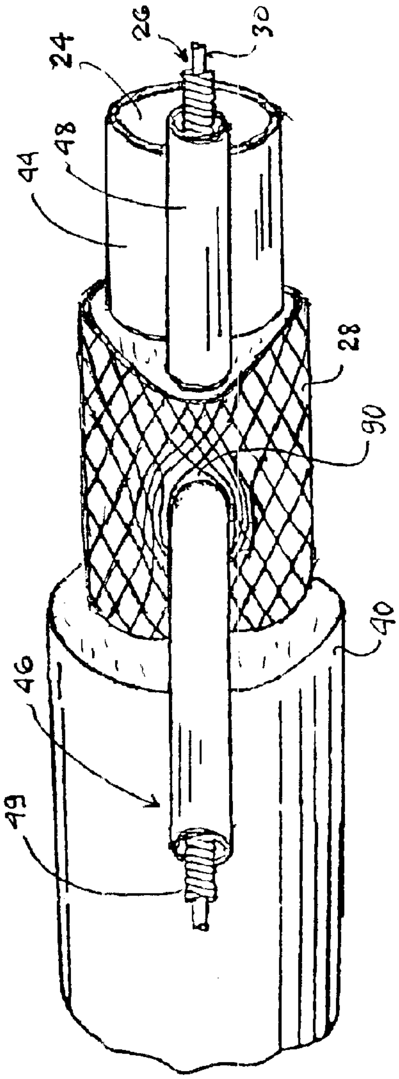
FIG. 7 is a side view of a portion of the proximal section of the catheter body depicting the wire braid port formed about the delivery lumen sheath enclosing the wire coil enclosing the pull wire.

Turning to FIGS. 6 and 7, it can be seen that the continuous wire braid 28 is formed of wires braided over the delivery lumen liner 44 and the pull wire lumen liner 46 distal to the pull wire jacket port 32, braided around the pull wire sleeve 48 to form a braid port 90, and braided over at least a portion of the delivery lumen liner 44 proximal to the pull wire jacket port 32. The wire braid 28 may be of a variety of different materials and configurations designed to impart the desired stiffness to the catheter shaft section and in particular ensure that the cross-sectional shape of the delivery and pull wire lumen liners 44 and 46 to remain substantially undistorted as the catheter body 12 undergoes high flexure encountered traversing sharp bends in the vascular or other anatomical pathway.

The wire braid 28 is depicted in an idealized manner in FIG. 2 as being tubular, such that the wire braid 28 appears to be circular in end view when wound about delivery lumen liner 44 and pull wire sheath 48. However, the wire braid is wound more tightly about the delivery lumen liner 44 and pull wire sheath 48 as shown in FIG. 7 so that the wire braid is not truly circular in end view. However, the outer wall of the catheter body through its length is preferably made circular in end view within specified tolerances by virtue of the reflow molding of the thermoplastic materials of the jackets 40, 41, 42 and 34 (and any other transition jackets) within heat shrink tube lumens as described herein.

The wire braid 28 constructions include metallic and non-metallic fibers or wires or ribbons that may be configured in a single or multiple spirals, braids or knits as is known in the art. Wire braid 28 can be formed of a metallic material, such as a superelastic alloy or stainless steel, or non-metallic materials such as those made of polyaramids, carbon fibers, Dacron, Nylon, or liquid crystal polymer and can even be made using natural fibers such as silk and cotton. The braid characteristics, such as pick, angle, spacing, the nature of the strand (i.e., flat or round), and the like, can be selected together with the characteristics of the thermoplastic proximal and intermediate jackets 40, 41, and 42 to provide a desired torsional stiffness and axial flexibility of the proximal, transition, and bendable intermediate sections 50, 51 and 52, respectively. The reinforcing and stiffening properties of the wire braid 28 allows the delivery lumen liner 44 and the pull wire lumen liner 46 to be formed of thin wall tubing maximizing lumen diameter and yet maintaining the integrity of the lumen cross-sectional shape.

During fabrication, the outer jacket 40 in proximal section 50, the outer jacket 41 in the transition section 51, the outer jacket 42 in intermediate section 52, and the distal jacket 34 in distal section 54 are heated to flow through the interstices of the wire braid 28 and about the outer surfaces of the pull wire lumen liner 46 and/or the delivery lumen liner 44 and to one another at the junctions 36, 37 and 38 of FIG. 2 as described further below. The tubular jackets 40, 41, 55 and 34 may be made from any suitable, biologically compatible, thermoplastic polymer, e.g., nylon, polyether block copolymers (e.g., Pebax® block copolymer s), polyolefins, and the like, typically having a hardness in the range from about 35D to 75D Shore durometer. Other possible polymers include polyethylene, polyurethane, polypropylene, polystyrene, polyethylene terephthalate, polyesters, polyvinyl chloride, silicone and lubricious polymers such as polyfluorocarbons or polysulfones.

The proximal jacket 40 can be formed preferably of one or more of Pebax® 7233 SA-00, Pebax® 7233 SA-01, Pebax® 7233 SN-00, Pebax® 7233 SN-01 polyether block copolymers having a 35D Shore durometer supplied by Atofina Chemicals, Inc., Philadelphia, Pa. Outer jacket 34 can be formed of Pebax® 6333 SA-00, Pebax® 6333 SA-01, Pebax® 6333 SN-00, Pebax® 6333 SN-01, Pebax® 5533 SA-00, Pebax® 5533 SA-01, Pebax® 5533 SN-00, Pebax® 5533 SN-01, Pebax® 4033 SA-00, Pebax® 4033 SA-01, Pebax® 4033 SN-00, Pebax® 4033 SN-01 polyether block copolymer s. Pellethane 2363 series or Tecothane polyurethane or Tecoflex® EG80A B20 polyether block copolymers could be used in a similar fashion. Tecoflex® EG80A B20 polyether block copolymers and Tecothane polyurethanes are made by Thermedics Polymer Products, Woburn, Mass.

Outer jackets 40, 41, 42 and 34 are preferably formed of 40D Shore durometer, 55D Shore durometer, 72D Shore durometer, and 55D Shore durometer Pebax® block copolymer s, respectively.

The delivery lumen liner 44 and the pull wire lumen sheath 48 preferably comprise relatively thin wall tubes formed of a durable material having a low coefficient of friction. For reflow manufacturing processes, the materials used to form the delivery lumen liner 44 and the pull wire lumen sheath 48 should adhere well with and have a higher melt temperature than the materials of jackets 40 and 42 that are reflowed around it. Suitable resins or polymers used to form the delivery lumen liner 44 and the pull wire lumen sheath 48 include polyurethane, high density polyethylene (HDPE), low density polyethylene (LDPE), polyvinylchloride (PVC), fluoropolymers including PTFE, vinylidene fluoride, polyimide, and their mixtures. Etching of the outer surfaces of the delivery lumen liner 44 and the pull wire lumen sheath 48 made from certain of these materials may be desirable to promote adhesion with the thermoplastic polymer selected to form the outer jackets 40 and 42. It may also be desirable to coat the lumen surfaces of the delivery lumen liner 44 and the pull wire lumen sheath 48 to increase lubricity with a lubricant, preferably a hydrophilic polyacrylamide. The polyacrylamide coating is preferably applied to the lumen surface by dipping or spraying or the like. The lumen diameter and wall thickness of the pull wire lumen sheath 48 and its specific properties may depend in part upon the diameter and type of wire coil 49 intended to be inserted into the pull wire lumen sheath lumen.

In a preferred embodiment, the delivery lumen liner 44 and the pull wire sheath 46 are formed of thin sidewall wall PTFE tubes that are surface etched on the exterior surfaces to promote adhesion with the Pebax® block polymers. The delivery lumen liner has an outer diameter of 0.024 inches (0.61 mm) and a wall thickness of 0.0005 inches (0.013 mm) to 0.0010 inches (0.025 mm). The pull wire sheath 46 has an outer diameter of 0.010 inches (0.025 mm) to 0.050 inches (1.25 mm) and a wall thickness of 0.0005 inches (0.013 mm) to 0.0010 inches (0.025 mm).

The wire coil 49 is preferably formed of flat wire having a wire width of 0.010 inches (0.254 mm) and a wire thickness of 0.0015 inches (0.0381 mm), wound to have a coil diameter of 0.016 inches (0.4064 mm) and a coil lumen diameter of 0.013 inches (0.3302 mm). The wire coil 49 preferably has a close wound wire coil proximal segment extending through the proximal section 50 from the junction 36 to the pull wire jacket port 32 so that the wire coil turns do not compress axially when the pull wire 30 is tensioned. The wire coil 49 preferably has a loose wound wire coil distal segment in the intermediate section 52 to allow such coil turn compression and to make it easier to bend the intermediate section 52 when the pull wire 30 is tensioned. The pull wire lumen 26 is defined by the wire coil lumen. The wire coil turns provide a hard and smooth bearing surface that the pull wire 30 readily moves against when it is tensioned.

The catheter body 12 can be between about 10 cm and 300 cm in length, but is typically and more preferably between about 30 cm and 150 cm in length. The catheter body 12 is preferably circular or slightly oval or triangular in cross-section and having a maximal outer diameter in the range of 4 French (0.44 mm) to 15 French (1.65 mm). Typically, proximal section 50 constitutes about 70–90% of the total length of catheter body 12, and relatively more flexible intermediate section 52 and distal section 54 constitute the remaining 10%–30% of the length of catheter body 12.

The pull wire 30 is preferably formed of 304 V stainless steel, 320–360 KPSI tensile strength, having a diameter of 0.011 inches (0.28 mm) to fit within the pull wire lumen 26. A distal segment of the pull wire 30 extending through the intermediate section 52 may be tapered or otherwise reduced in diameter to a dimension of 0.016 inches (0.41 mm) wide and 0.0065 inches (0.17 mm) thick, for example, to make the intermediate section 52 easier to bend. During assembly as described further below, the proximal end of a pull wire 30 having a pull wire ring attached to the pull wire distal end is inserted through the wire coil lumen distal exit port and advanced proximally through the length of the wire coil lumen within the catheter body 12 and out of the pull wire jacket port 32.

Figure 3:
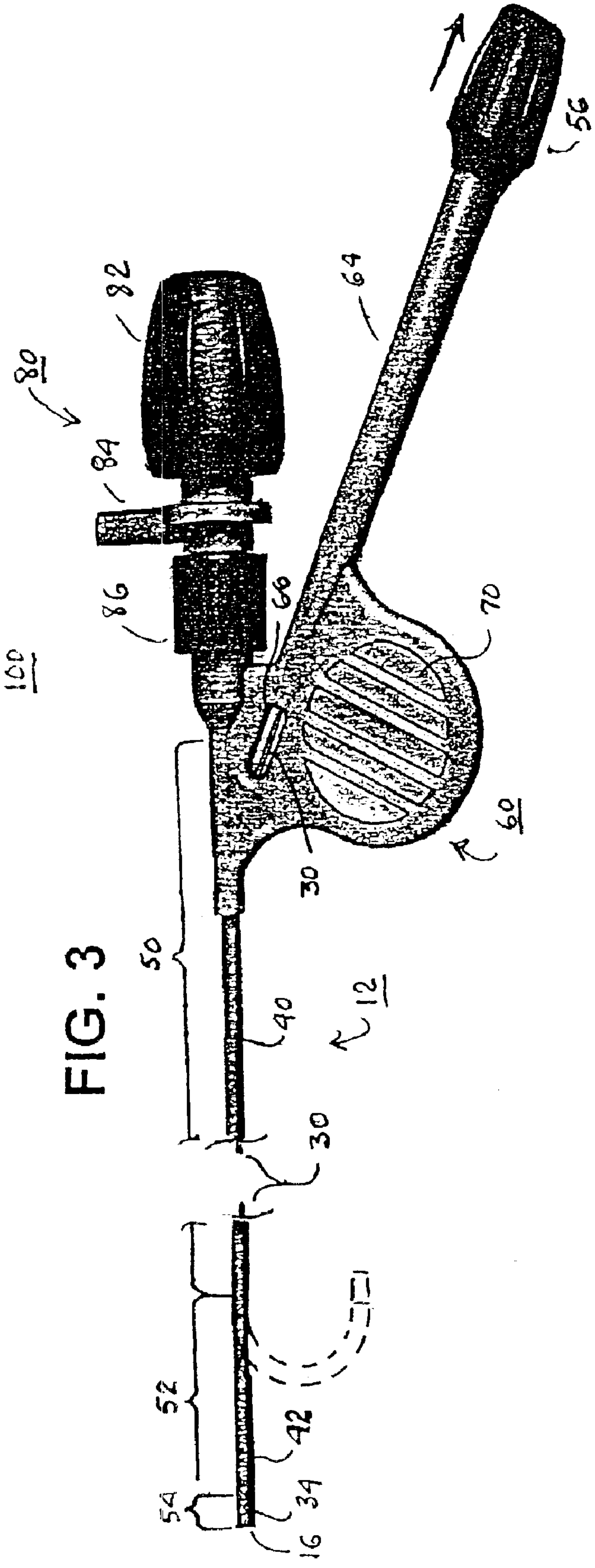
FIG. 3 is a plan view of a pull wire operated steerable catheter formed of the catheter body of FIGS. 1 and 2 and a universal hub.
Figure 4:
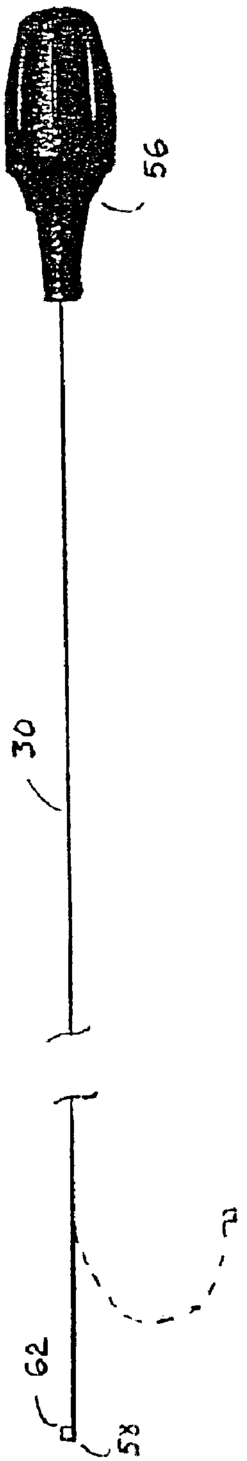
FIG. 4 is a plan view of the pull wire employed in the pull wire operated steerable catheter of FIG. 3.

The catheter body 12 can be mated with a wide variety of proximal handles or hubs to form a steerable catheter, and one example of a steerable catheter 100 formed of the catheter body 12 and a hub 60 and hemostasis valve 80 is depicted in FIG. 3. An exemplary pull wire 30 adapted to be used with the particular hub 60 is depicted in FIG. 4. The exemplary pull wire 30 depicted in FIG. 4 extends between a proximal pull wire knob 56 attached to and enclosing the pull wire proximal end and a radiopaque band 62 attached, e.g., by welding, to the pull wire distal end 58. Radiopaque band 62 is embedded within a polymeric retention sheath over the wire braid proximal to the catheter body distal end 16 in a manner described further below.

The hub 60 comprises a molded hub body enclosing a hub delivery lumen and a hub pull wire lumen within a hub extension 64 diverging apart from one another. The catheter body proximal end 14 and a distal portion of the proximal section 50 are received within an enlarged common hub lumen that is axially aligned with a hemostasis valve lumen within hemostasis valve 80. The delivery lumen 24 is thereby axially aligned with the hemostasis valve lumen, and the pull wire jacket port 32 is aligned with the hub pull wire lumen. The proximal section of the pull wire 30 exiting the pull wire jacket port 32 is extended through a window 66 and the hub pull wire lumen within the hub extension 64. The pull wire handle 56 is then affixed to the pull wire proximal end.

The hemostasis valve 80 comprises a proximal rotating closure knob 82, an intermediate side port 84 for attachment to an extension hose and stopcock (not shown), and a distal rotating locking collar 86 for securing a valve to a luer hub fitting 86. The knob 82, side port 84, and collar 86 constitute a standard hemostasis valve 80 to introduce or aspirate fluids into or from the delivery lumen or to enable insertion of a cardiac lead or other implantable or diagnostic elongated medical device into the delivery lumen.

An enlarged, relatively flat paddle 70 is formed extending away from the hub delivery lumen and hub extension 64 that can be gripped on either side by the fingers to assist in holding and manipulating the hub 60 during use of the catheter 100. The pull wire knob 56 can be pulled away from the side branch 64 to induce the bend in the intermediate section 52 depicted in broken lines.

Figure 5:
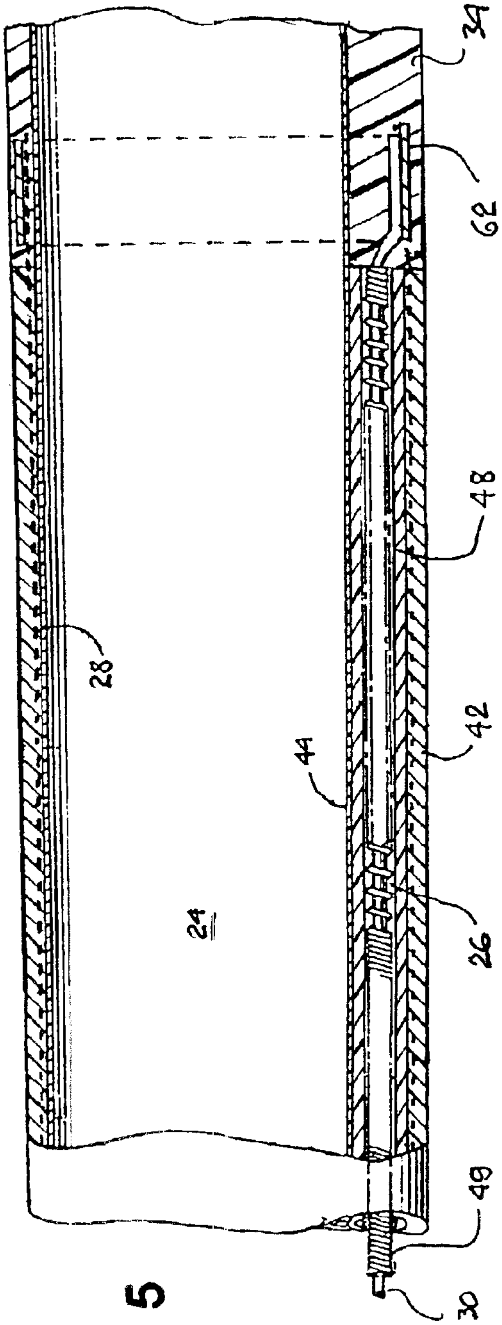
FIG. 5 is a cross-section view of a portion of the distal segment of the catheter body of FIG. 3 illustrating the fixation of the pull wire to the internally disposed wire braid overlying the side-by-side aligned deflection lumen and delivery lumen proximal to the catheter body distal end.

Turning to FIG. 5, it depicts the construction of the distal and intermediate catheter body sections 50 and 52 in greater detail, particularly the radiopaque marker band 62 about the distal end of the wire braid 28 to hold it in place and prevent flaring of the cut wire ends. In accordance with one feature of the present invention, a high tensile strength wire is employed to form the wire braid 28 woven about the pull wire lumen liner 46 and/or the delivery lumen liner 44 that is entrapped mechanically at the catheter body distal end. Torqueability of the catheter body through the entire wire braid reinforced catheter body length is not negatively affected by annealing the wire braid during the fabrication process, since annealing is not necessary. The band 62 is preferably radiopaque to provide a marker band visible under fluoroscopy.

As shown in FIG. 5, the depicted wire coil 49 has a close wound wire coil proximal segment extending through the proximal section 50 from the junction 36 to the pull wire jacket port 32 so that the wire coil turns do not compress axially when the pull wire 30 is tensioned. The wire coil 49 preferably has a loose wound wire coil distal segment in the intermediate section 52 to allow such coil turn compression and to make it easier to bend the intermediate section 52 when the pull wire 30 is tensioned.

The wire braid port 90 and pull wire jacket port 32 are depicted in FIGS. 6 and 7. The wires of the wire braid 28 are woven tightly about the delivery lumen liner 44 and the pull wire lumen sheath 48 distal to the wire braid port 90 during the manufacturing process in a manner described further herein. The wires of the wire braid 28 are woven tightly about the delivery lumen liner 44 proximal to the wire braid port 90. The woven wires are diverted around the pull wire lumen sheath 48 but are not severed in the process so that the wire braid is not rendered discontinuous between the proximal and distal ends of the wire braid 28 simply due to the formation of the wire braid port. The formation of the wire braid port advantageously eliminates the necessity of trying to cut through or divert the wires or the wire braid to locate the pull wire after formation of the proximal outer sheath 50 and the attendant ruining of the finished catheter body if a mistake is made.

A preferred manufacturing method of manufacturing a catheter from the catheter body 12 and a catheter hub is depicted in FIGS. 9-13. The top level manufacturing method depicted in FIG. 9 comprises the steps of forming the wire-braided sub-assembly (step S100), inserting and fixing the pull wire in the wire-braided sub-assembly (step S200), forming the outer jacket in the proximal and intermediate sections 50 and 52 (step S300), forming the distal section 34 (FIG. S400), and the catheter body 12 is joined with a catheter hub of any preferred type in step S500. Step S500 can be performed in any of the known ways employing any configuration of a catheter hub, e.g., catheter hub 60 of FIG. 3 (to form catheter 100 in that depicted example). Steps S100, S200, S300 and S400 are depicted in greater detail in FIGS. 10–13.

Figure 10:
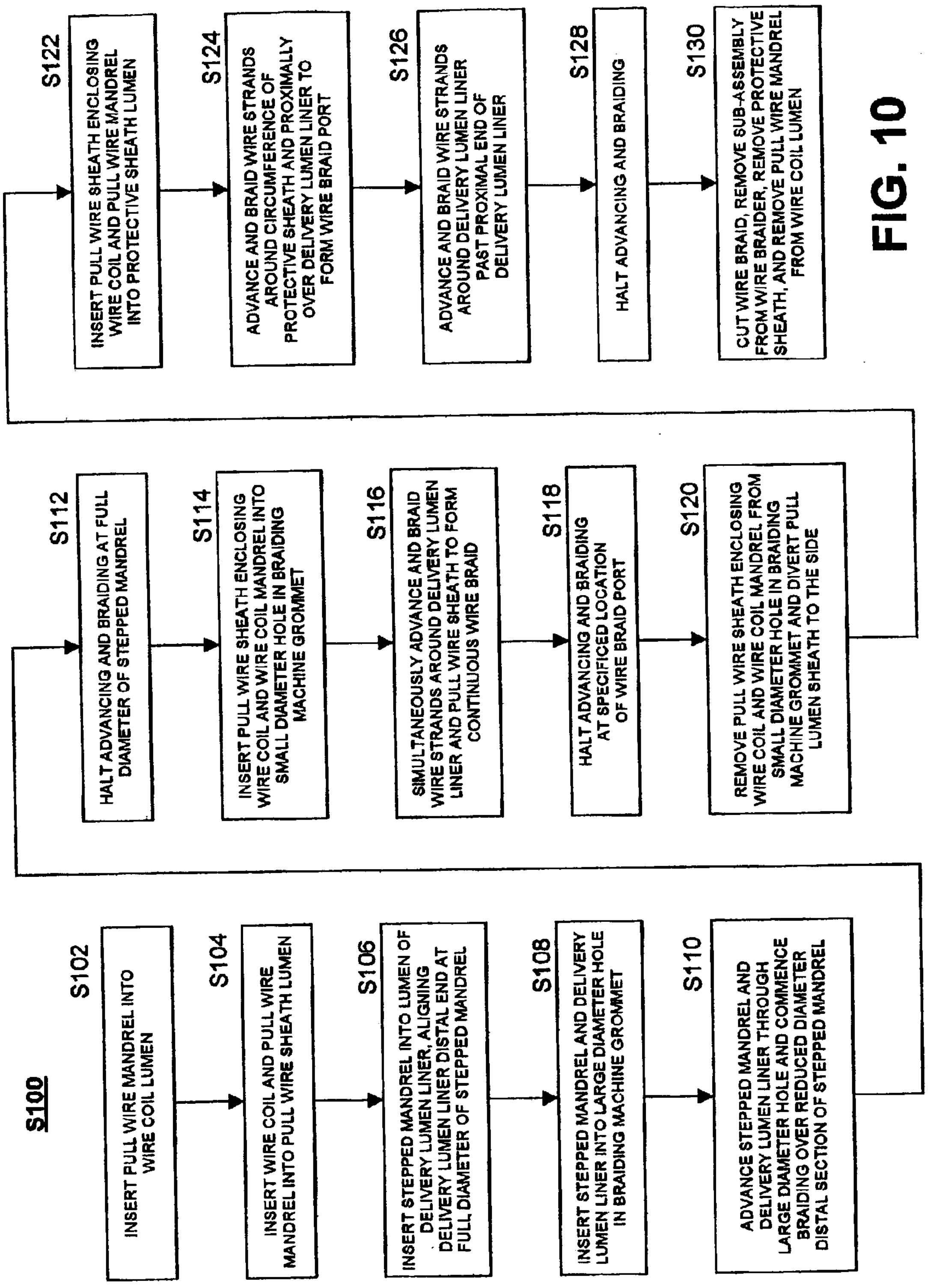
FIG. 10 is a detailed flow chart illustrating the steps of step S100 of FIG. 9.

Turning to FIG. 10, the wire braiding of the wire braid 28 is preferably accomplished using an automated braiding machine, e.g., a STEEGER® Model K80-72# horizontal fine wire braider that can braid between 3 and 216 or more strands of metal ribbon wire having a thickness between 0.0005 inches (0.0127 mm) and 0.003 inches (0.00762 mm) and a width between 0.0025 inches (0.00635 mm) and 0.01 inches (0.0254 mm), or alternatively round, D-shaped, or other wire with diameter between 0.0005 inches (0.0127 mm) and 0.005 inches (0.127 mm). Preferably for the dimensions and materials described herein, the wire braider braids 45 picks of wires formed of 16 ribbon wires, having dimensions of 0.001 inches (0.0254 mm) thick and 0.005 inches (0.127 mm) wide.

Figure 8:
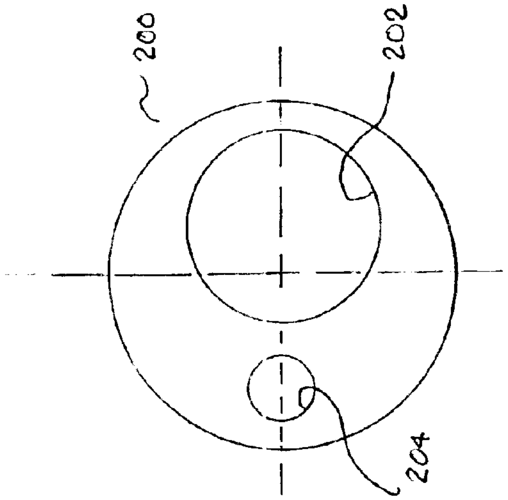
FIG. 8 is an end view of a braiding machine grommet depicting a large diameter grommet hole and small diameter grommet hole through which the delivery lumen liner and mandrel are inserted and the pull wire lumen liner and mandrel are inserted, respectively, in the wire braiding process.

Typically, such wire braiders braid wire strands into wire braid over a single lumen liner supported by a mandrel that is passed into the braiding region of the wire braider through a hole of an input cone or grommet. The wire-braided lumen liner exits the braiding region through a similar hole of an output cone. An input grommet 200 employed in forming the wire-braided sub-assembly of the present invention is depicted in FIG. 8. The grommet 200 has a first hole 202 through which the mandrel supported delivery lumen liner 44 is passed and a second hole 204 through which the mandrel supported pull wire sheath 48 is passed.

First, the wire coil 49, pull wire sheath 48 and pull wire mandrel (not shown) are assembled in steps S102 and S104, and a stepped diameter delivery mandrel is inserted into the delivery lumen liner lumen 24 in step S106 in no particular order. In step S102, the pull wire mandrel is inserted into the wire coil lumen and the wire coil and wire coil mandrel are inserted into the pull wire sheath lumen. The pull wire sheath distal end is aligned to the wire coil distal end, and the relative positions can be maintained by use of an adhesive. In step S106, the distal end of the delivery lumen liner and the distal end of the stepped mandrel are aligned such that a distal portion of the delivery lumen liner is distal to the step from the mandrel full diameter to the reduced diameter of the mandrel.

In step S108, the distal end of the stepped mandrel is inserted through the hole 202 of the entry grommet 200, and wire braiding over the reduced diameter distal section of the mandrel is commenced in step S110 at 45 picks per inch, for example. Braiding is halted or paused in step S112 when the braid reaches the full diameter of the stepped mandrel. The step change in diameter of the mandrel is marked so that the step is visible to the operator through the translucent delivery lumen liner 44 and the wire braid. The distal end of the mandrel supported pull wire sheath and pull wire coil are then inserted in step S114 through the small diameter hole 204 in the braid input grommet 200 and advanced into alignment with the step.

Then, in step S116, braiding is restarted while the mandrel supported, pull wire lumen liner and the delivery lumen liner are advanced side-by-side through the braiding region. Braiding is halted or paused at a specified distance, e.g., ~112 cm, in step S118. The relatively short proximal segment of the mandrel supported pull wire liner 46 including pull wire sheath 48 and wire coil 49 is pulled through the small diameter hole 204 and diverted away from the side-by-side relation with the mandrel supported delivery lumen liner 44 in step S120. The mandrel supported pull wire liner 46 including pull wire sheath 48 and wire coil 49 are inserted through the lumen of a protective sheath, e.g., a short length of hypotube in step S122. The braiding and advancement of the delivery lumen liner 44 through the braiding region is restarted in step S124. The plurality of wires are then braided in step S126 into the continuous wire braid extending around the diverted proximal segment of the pull wire lumen liner 44 to form the wire braid port 90 shown in FIG. 7. Braiding is continued in step S126 until the proximal end of the delivery lumen liner 44 exits the braider output cone. Braiding is then halted in step S128, and the proximal end of the wire braid is cut, the wire-braided sub-assembly is removed from the braider, and the pull wire mandrel is removed from the wire coil lumen in step S130.

Figure 11:
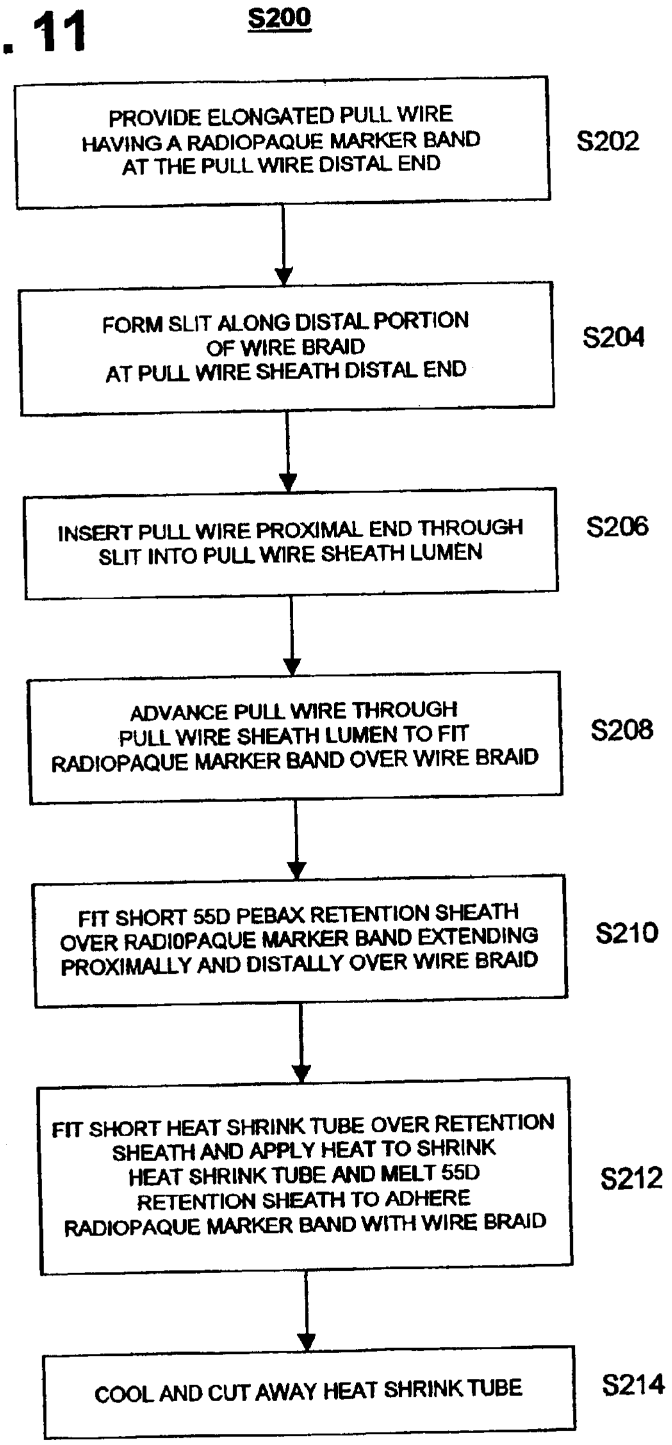
FIG. 11 is a detailed flow chart illustrating the steps of step S200 of FIG. 9.
Figure 9:
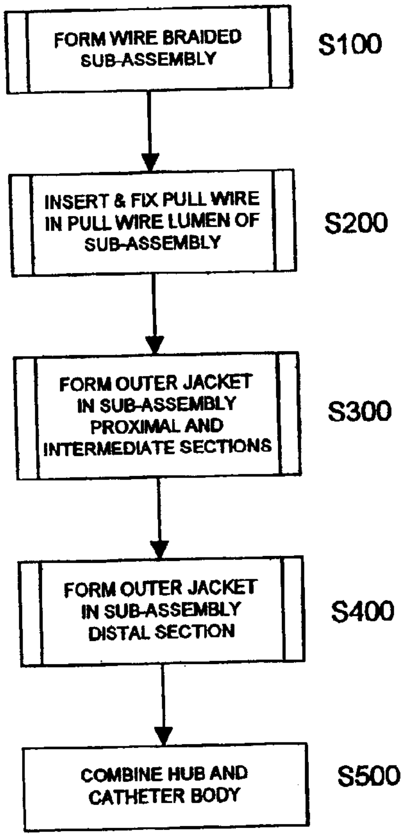
FIG. 9 is a top-level flow chart illustrating the method steps of manufacturing a catheter body in accordance with the present invention.

The pull wire 30 is then assembled into the wire coil lumen in step S200 shown in FIG. 11. In step S202, the elongated pull wire 30 is provided with the marker band 62 welded to the pull wire distal end. The pull wire 30 may be tapered or stepped down in diameter in the distal section 52. A slit is formed in a distal length of the wire braid 28 just distal to the pull wire sheath end to access the pull wire lumen 26 defined by the wire coil lumen in step S204. The pull wire proximal end is inserted into the pull wire lumen 26 and advanced distally in step S208 until the radiopaque band 62 can be fitted over the wire braid and lodged overlying the wire braid 28 over the delivery lumen liner 44 just distal to the distal end of the pull wire sheath 48.

The radiopaque band 62 is then cemented in place in a reflow process of a short retention sheath. A short length of thermoplastic tubing, e.g., 55D Pebax®, is fitted over the radiopaque band 62 extending over the exposed wire braid 28 proximally and distally from the radiopaque band 62 in step S210. A short length of FEP heat shrink tube is fitted over the retention sheath, and heat is applied in step S212 to shrink the heat shrink material and melt the 55D Pebax® to cause it to flow into the wire braid 28 and form a thin film over the radiopaque band 62. After cooling, the heat shrink tube is cut away in step S214.

Figure 12:
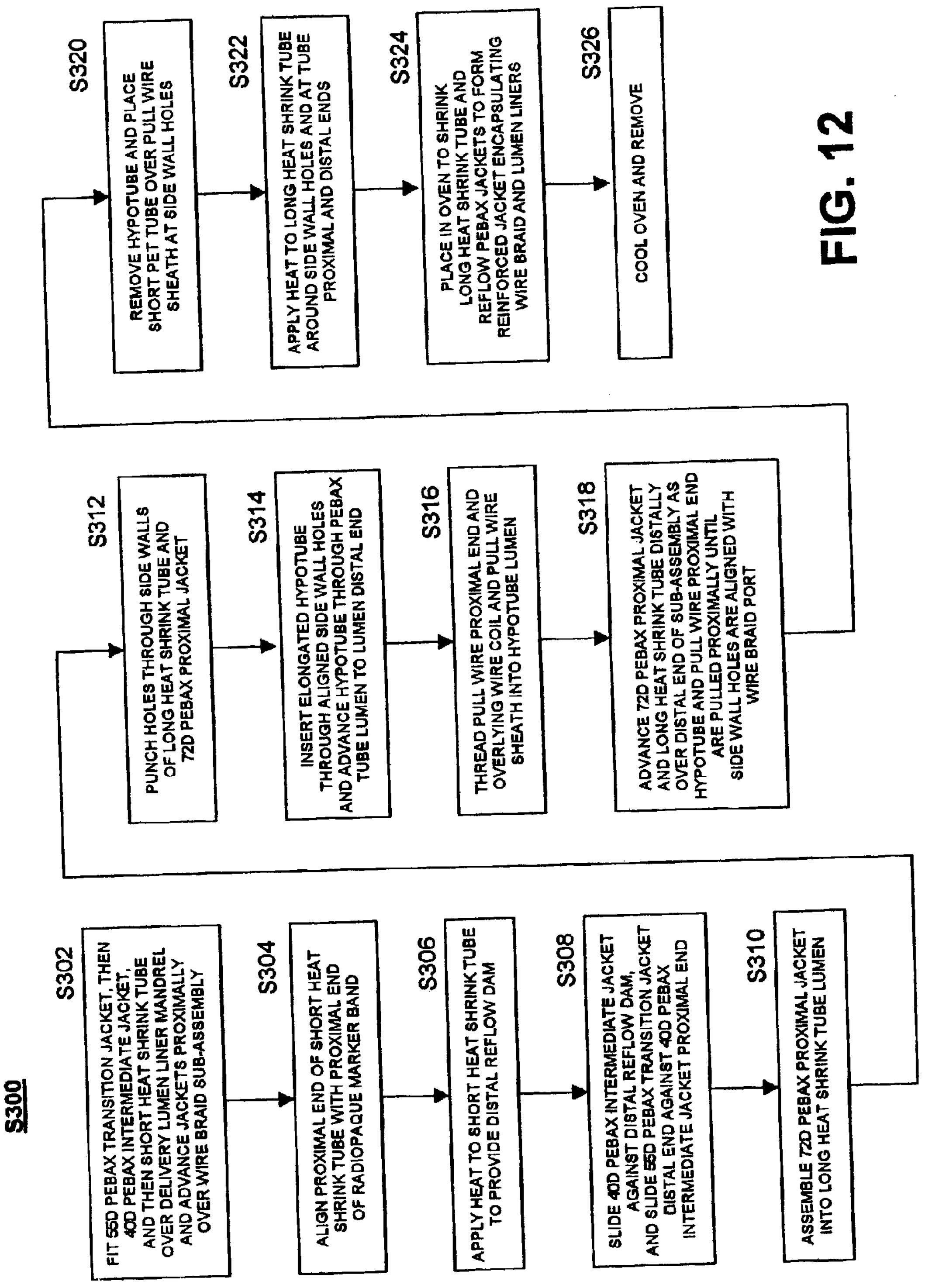
FIG. 12 is a detailed flow chart illustrating the steps of step S300 of FIG. 9.

The outer sheath or jacket in the transition and intermediate sections 51 and 52 is formed of the jackets 41 and 42 in step S300 shown in FIG. 12. In step S302, the 55D Pebax® block copolymer transition jacket 41, and the 40D intermediate short 55D Pebax® block copolymer transition jacket, and a short heat shrink tube are successively inserted over the distal end delivery lumen mandrel and advanced proximally in step S302. The proximal end of the short heat shrink tube is aligned to the proximal end of the radiopaque band 62 and heated to shrink against the heat shrink band to provide a distal reflow dam in step S306. The 55D Pebax® block copolymer intermediate jacket 42 and the short 55D Pebax® block copolymer transition jacket 41 are stacked against the distal reflow dam in step S308.

In step S310, a relatively long 72D Pebax® block copolymer proximal jacket 40 is fitted into a long heat shrink tube lumen so that the heat shrink tube has a distal segment long enough to extend over intermediate and transition jackets. In step S312, holes are punched through the sidewalls of the relatively long 72D Pebax® block copolymer proximal jacket 40 and the long heat shrink tube at locations along their lengths that will be aligned with the location of the wire braid port 90. It is then necessary to thread the proximal segment of the wire-braided sub-assembly proximal end first through the distal end opening of the lumen of the relatively long 72D Pebax® block copolymer proximal jacket 40. The proximal ends of the pull wire lumen liner 46 and pull wire 30 are to be threaded from within the lumen of the relatively long 72D Pebax® block copolymer proximal jacket 40 through the aligned holes to the exterior of the long heat shrink tube. The distal end of the relatively long 72D Pebax® block copolymer proximal jacket 40 is to then abut the proximal end of the 55D Pebax® block copolymer jacket 42, and the long heat shrink tube is to overlie the distal reflow dam.

Thus, in step S314, an elongated hypotube is inserted through the aligned sidewall holes and the lumen of the relatively long 72D Pebax® block copolymer proximal jacket 40 to exit the distal end opening thereof. The hypotube enclosing the proximal section of the pull wire lumen liner 46 and pull wire 30 are threaded through the hypotube lumen in step S316 as the long 72D Pebax® block copolymer proximal jacket 40 and the long heat shrink tube are advanced distally over the wire-braided sub-assembly in step S318. The hypotube is removed, and a short heat protective tube of PET is fitted over the pull wire lumen liner 46 and pull wire 30 in step S320.

Heat is then applied in step S322 by heat gun to the area around the wire braid port 90 and the proximal and distal ends of the long heat shrink tube to hold the parts together. A number of catheter body assemblies fabricated in this manner are then hung on a fixture within a heat chamber of an industrial oven and heated to shrink the long heat tubes and reflow the proximal and intermediate jackets in step S324 and then cooled in step S326.

It is then necessary to reflow the distal jacket 34 about the distal section 54 or the catheter body in step S400. In steps S402 and S404, the distal portion of the long heat shrink tube is cut away, and the underlying reflow dam is cut away. Then, the wire braid 28 distal to the radiopaque marker band 62 is roll cut away and removed from the delivery lumen mandrel, exposing the distal section of the delivery lumen liner 44 in step S406. A short 55D Pebax® block copolymer distal jacket 34 is then fitted over the radiopaque marker band 62 abutted proximally against the transition jacket and extending distally over the distal section of the delivery lumen liner in step S408. A further short heat shrink tube is fitted over the delivery lumen liner and shrunk in place to act as a further reflow dam in step S410. A further heat shrink tube is fitted over the distal segment including the distal jacket 34 in step S412. Heat is applied to shrink the heat shrink tube and reflow the distal jacket 34 with the transition jacket and over the delivery lumen liner and radiopaque marker band 62 in step S414.

After cooling, the heat shrink tube and the reflow dam are cut away in step S416, and the PET sleeve is removed from over the pull wire lumen liner in step S418. The proximal end of the catheter body is then trimmed away from the delivery lumen mandrel in steps S420 and S422 in preparation for removal of the mandrel and long heat shrink tube. A fixture is used to grip the delivery lumen liner and allow its removal in step S424. Then, the remaining long heat shrink tube is removed in step S426, and the pull wire is exposed at the pull wire port jacket port 32 in step S428. The catheter body 12 is then cleaned, inspected and ready for assembly with the catheter hub in step S500 of FIG. 9.

All patents and publications identified herein are hereby incorporated by reference in their entireties.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A steerable catheter comprising a catheter hub and an elongated catheter body having a catheter body sidewall extending between a catheter body proximal end and a catheter body distal end, the catheter body further comprising: p1 a delivery lumen liner having a delivery lumen extending between a delivery lumen entry port and a delivery lumen exit port at the catheter body distal end;

a pull wire lumen liner having a pull wire lumen extending between a pull wire jacket port through the sidewall of the catheter body and a pull wire lumen distal end;

a pull wire extend big from a pull wire proximal end through the pull wire jacket port and through the pull wire lumen to a pull wire distal end fixed to the catheter body at the pull wire lumen distal end;

a continuous wire braid formed of wires braided over the delivery lumen liner and the pull wire lumen liner distal to the pull wire jacket port, braided around the pull wire jacket port to form a braid port, and braided over at least a portion of the delivery lumen liner proximal to the pull wire jacket port; and a polymeric sheath encapsulating the wire braid around the delivery lumen liner and the pull wire lumen liner.

2. The steerable catheter of claim 1, wherein the polymeric sheath is formed of a series of thermoplastic materials having durometers that are progressively softer distally that are thermally bonded to the wire braid, the delivery lumen liner, and the pull wire lumen liner.

3. The steerable catheter of claim 1, wherein the pull wire lumen liner comprises a wire coil having a wire coil lumen defining the pull wire lumen.

4. The steerable catheter of claim 1, wherein the pull wire lumen liner comprises a wire coil having close wound wire coil turns in a wire coil proximal segment and loose wound wire coil turns in a wire coil distal segment.

5. The steerable catheter of claim 1, wherein the pull wire lumen liner comprises a pull wire lumen sheath having a pull wire lumen sheath lumen and a wire coil fitted into the pull wire lumen sheath and having a wire coil lumen defining the pull wire lumen.

6. The steerable catheter of claim 1, wherein the pull wire lumen liner comprises a pull wire lumen sheath having a pull wire lumen sheath lumen and a wire coil fitted into the pull wire lumen sheath and having a wire coil lumen defining the pull wire lumen, the wire coil having close wound wire coil turns in a wire coil proximal segment and loose wound wire coil turns in a wire coil distal segment.

7. The steerable catheter of claim 1, wherein the pull wire further comprises a band attached to the pull wire distal end and embedded within a polymeric sheath over the wire braid proximal to the catheter body distal end.

8. The steerable catheter of claim 7, wherein the wire braid wires are formed of high tensile strength materials and extend from the catheter body proximal end to the band attached to the pull wire distal end, and the band is fitted over a distal segment of the wire braid and restrains distal ends of the wires from flaring away from the delivery lumen liner.

9. A steerable catheter comprising a catheter hub and an elongated catheter body having a catheter body sidewall extending between a catheter body proximal end and a catheter body distal end, the catheter body further comprising:

a delivery lumen liner having a delivery lumen extending between a delivery lumen entry port and a delivery lumen exit port at the catheter body distal end;

a pull wire lumen liner having a pull wire lumen extending between a pull wire lumen port of the catheter body and a pull wire lumen distal end;

a wire braid formed of high tensile wires braided over the delivery lumen liner and the pull wire lumen liner, the wires extending between wire proximal ends and wire distal ends;

a pull wire extending from a pull wire proximal end through the pull wire lumen port and through the pull wire lumen to a pull wire distal end;

a band attached to the pull wire distal end and fitted over a distal segment of the wire braid proximal to the catheter body distal end to fix the pull wire distal end to the catheter body and to restrain the wire distal end from flaring away from the delivery lumen liner; and a polymeric sheath encapsulating the wire braid and the delivery lumen liner and the pull wire lumen liner within the wire braid.

10. The steerable catheter of claim 9, wherein the polymeric sheath is formed of a series of thermoplastic materials having durometers that are progressively softer distally that are thermally bonded to the wire braid, the delivery lumen liner, and the pull wire lumen liner.

11. The steerable catheter of claim 9, wherein the pull wire lumen liner comprises a wire coil having close wound wire coil turns in a wire coil proximal segment and loose wound wire coil turns in a wire coil distal segment.

12. The steerable catheter of claim 9, wherein the pull wire lumen liner comprises a wire coil having a wire coil lumen defining the pull wire lumen.

13. The steerable catheter of claim 9, wherein the pull wire lumen liner comprises a pull wire lumen sheath having a pull wire lumen sheath lumen and a wire coil fitted into the pull wire lumen sheath and having a wire coil lumen defining the pull wire lumen.

14. The steerable catheter of claim 9, wherein the pull wire lumen liner comprises a pull wire lumen sheath having a pull wire lumen sheath lumen and a wire coil fitted into the pull wire lumen sheath and having a wire coil lumen defining the pull wire lumen, the wire coil having close wound wire coil turns in a wire coil proximal segment and loose wound wire coil turns in a wire coil distal segment.

* * * * *

UNITED STATES PATENT AND TRADEMARK OFFICE

CERTIFICATE OF CORRECTION

PATENT NO. : 6,945,956 B2
APPLICATION NO. : 10/328329
DATED : September 20, 2005
INVENTOR(S) : Waldhauser et al.

It is certified that error appears in the above-identified patent and that said Letters Patent is hereby corrected as shown below:

Col. 16, line 32, delete "p1 a delivery lumen liner…" and insert --A delivery lumen liner…--

Signed and Sealed this

Twentieth Day of March, 2007

JON W. DUDAS

*Director of the United States Patent and Trademark Office*